United States Patent [19]

Stone et al.

[11] Patent Number: 5,284,843
[45] Date of Patent: Feb. 8, 1994

[54] PHARMACOLOGICAL TREATMENT OF OCULAR DEVELOPMENT

[75] Inventors: Richard A. Stone, Havertown; Alan M. Laties, Philadelphia, both of Pa.; Paul M. Iuvone, DeKalb, Ga.

[73] Assignees: Trustees of the University of Penna., Philadelphia, Pa.; Emory University, Atlanta, Ga.

[21] Appl. No.: 687,847

[22] Filed: Apr. 10, 1991

Related U.S. Application Data

[63] Continuation of Ser. No. 342,942, Apr. 25, 1989, abandoned, which is a continuation-in-part of Ser. No. 202,220, Jun. 3, 1988, abandoned.

[51] Int. Cl.$^5$ .................... A61K 31/55; A61K 31/44
[52] U.S. Cl. .................................. 514/213; 514/284; 514/293; 514/297; 514/912
[58] Field of Search ............... 514/213, 293, 284, 297, 514/912

[56] References Cited

PUBLICATIONS

The Merck Index tenth Edition, p. 772 (1983).
Soc Neuyosci. Abst. vol 13, part 1, p. 240, 1987.

*Primary Examiner*—Zohreh A. Fay
*Attorney, Agent, or Firm*—Woodcock Washburn Kurtz MacKiewicz & Norris

[57] ABSTRACT

A method of inhibiting the abnormal postnatal axial growth of the eye of a maturing animal during conditions ordinarily leading to said abnormal growth, which comprises (1) determining the neurochemical present in the retina of said eye, eg., dopamine, the concentrations of which is reduced during said conditions, and (2) administering to said eye during post natal maturation effective amounts of said neurochemical, its agonist or its antagonist.

14 Claims, No Drawings

PHARMACOLOGICAL TREATMENT OF OCULAR DEVELOPMENT

GOVERNMENT SUPPORT

Portions of this invention were supported by National Eye Institute grants R01-EY-05454 and R01-EY-04864.

This is a continuation of application Ser. No. 342,942, filed Apr. 25, 1989, abandoned which in turn, is a continuation-in-part of Ser. No. 202,220, filed Jun. 3, 1988, now abandoned.

BACKGROUND OF THE INVENTION

This invention relates to control of ocular development and, more particularly, to the treatment of the eye to control the development of myopia (commonly known as nearsightedness).

It has been estimated that about one of every four persons on earth suffers from myopia. About one-half or more of these cases are axial myopia, i.e., an elongation of the eye along the visual axis.

At birth, the human eye is about two-thirds adult size and is even at that size relatively short in the axial direction. As a consequence, young children tend to be farsighted. During childhood, as the eye grows, there is a compensatory fine tuning of the optical properties of the cornea and lens to the increasing ocular length. Often the entire process is virtually perfect and no correction is needed for sharp vision at distance; the eye is emmetropic. When regulatory failure in this finely tuned process occurs, it usually goes toward a lengthened eye. As a result, distant images focus in front of the plane of the retina and axial myopia results. If, on the other hand, the regulatory failure leads to an eye whose ocular length is too short, near images focus behind the plane of the retina and the result is hyperopia (commonly known as farsightedness).

Over the years, many theories have been put forth to explain the development of myopia, e.g., inheritance, excessive near work, and environmental influences such as hours of sunshine, diet, etc. From these theories many preventative measures have been proposed including spectacles, eye exercise, eye rest, cycloplegia, and other drug therapies. The clinical literature on the subject is massive.

Based on a theory that substantial use of the eye by children for reading leads to the development of permanent nearsightedness or myopia, many remedies directed at the focussing mechanism at the front of the eye have been proposed. Largely these have been attempts either to block near focus through topical application of drugs or to remove any need for near focus through use of plus lenses that in effect perform the near focus task. Topical drugs that relax the focussing muscle of the eye, the ciliary muscle, are called cycloplegics and have been available for a century.

Some clinical studies have suggested that atropine, a long-acting cycloplegic, applied topically to the eye may retard development of myopia. Atropine treatment, however, is not practical: it causes dilation of the pupil, which results in light sensitivity, and its action to inhibit ocular focussing impairs near visual work like reading. In addition to the discomfort to the patient, there are indications that excess light can harm the retina and questions have been raised concerning the danger of the long-term use of atropine (or other strong cycloplegics) on the retina when exposed to bright light.

There is now substantial evidence to link the posterior part of the eye, specifically image quality at the retina and hence the nervous system, to the postnatal regulation of ocular growth. There is significant evidence of myopia resulting in an eye that is subjected to retinal image degradation. It has been shown that axial myopia can be experimentally induced, in either birds or primates, in an eye in which the retina is deprived of formed images, e.g., by suturing the eyelids. The experimental myopia induced in primates such as monkeys precisely mimics the common axial myopia of humans.

Thus, the phenomenon of an animal's vision process apparently contributes to the feedback mechanism by which postnatal ocular growth is normally regulated and refractive error is determined. This indicates that this mechanism is neural and likely originates in the retina.

SUMMARY OF THE INVENTION

It has been found in accordance with this invention that the growth of an animal's eye can be inhibited or regulated by pharmacologically controlling the changes in the eye's neurochemistry. This invention is more particularly pointed out in the appended claims and described in its preferred embodiments in the following description.

DETAILED DESCRIPTION OF THE INVENTION

In the ordinary visual function of the eye of an animal, light forming an image passes through the lens and is received by the retina. The retina transmits this information to the optic nerve which sends it on to the brain.

Retinal neurochemicals (i.e., neuro-active chemical compounds) are key ingredients in the vision process. Specifically, light forming the image is sensed by the light receptors, the rods and cones, of the retina. These receptors act as transducers changing light energy into electrical and/or chemical signals.

In the regular process of transmitting the image information to the brain, retinal nerve cells, in association with the photo receptors, release neurochemicals to pass information to adjacent retinal cells as parts of a network in the retina leading to the optic nerve.

When the eye of an animal during its postnatal growth period is deprived of vision (e.g., by suturing eyelids) or otherwise subjected to retinal image degradation, the result ordinarily is abnormal ocular growth leading to myopia. During this period of image deprivation or degradation, it has been found that the metabolism of certain retinal neurochemicals is altered leading to changes in retinal concentrations thereof.

Specifically, it was noted that during periods of ocular image deprivation in maturing birds or primates, chemical alterations take place in the retina concurrent with the excessive ocular growth leading to myopia. These chemical alterations include reduced retinal concentrations of the neurochemical dopamine, and its metabolite 3,4-dihydroxyphenylacetic acid (DOPAC). In contrast, the concentration of the neurochemical serotonin in the retina is apparently not significantly changed during this time.

It has been found in accordance with this invention that the ocular administration of dopamine-related agents, such as apomorphine (an agonist) or the butyrophenone, haloperidol (an antagonist) to the eye of a young, maturing animal can inhibit, and in some cases completely prevent, the axial enlargement of the eye subjected to conditions ordinarily leading to ocular enlargement.

Broadly stated, it appears that the development of myopia in the eye of an animal can be inhibited by the postnatal ocular control of the presence of a neurochemical or an agonist or antagonist of the neurochemical, which neurochemical is found to be altered under conditions during maturation ordinarily leading to myopia. Prevention (treatment) of myopia can be accomplished by the administration of the neurochemical, its agonist or antagonist; it could also be accomplished by administration of drugs that otherwise interact with the synthesis, storage, release, receptor interaction, reuptake, or degradation of the naturally-occurring neurochemical, thus influencing the tissue levels and/or bioavailability of the naturally-occurring neurochemical. Examples of each of the more indirect drug activities are provided with reference to dopaminergic neural mechanisms as now understood for the central nervous system (of which the retina is a part). For instance, enzymatic synthesis can be stimulated by administration of levodopa or pteridine cofactor or can be inhibited by α-methyl-paratyrosine. Representative drugs that interfere with dopamine storage are reserpine and tetrabenazine, the latter of which also interferes with the dopamine uptake mechanism. Drugs that influence dopamine release mechanisms include those that stimulate release (e.g., high doses of amphetamine) and those that inhibit release (e.g., δ-hydroxy-butyrate). For receptor interaction, the discussion below deals mostly with post-synaptic receptor sites; it is also anticipated that drugs influencing pre-synaptic or auto-receptor sites will be active; apomorphine in fact seems to have auto-receptor properties in addition to its post-synaptic actions. As illustrations, 3-PPP (3-(3-hydroxyphenyl)-N-n-propylpiperindine) and TL-99 (6,7-dihydroxy-2-dimethylaminotetralin) are selective auto-receptor agonists. Agents that might influence the reuptake of released neurotransmitter are illustrated by those now known to interfere with dopamine reuptake into the pre-synaptic nerve terminal: amphetamine (in lower doses), benztropine and amitriptyline. Neurotransmitters after release can be degraded by enzymes. For the dopamine system, available drugs inhibit the activity of two enzymes that are involved with dopamine degradation: monoamine oxidase is inhibited by tranycypromine and pargyline, clorgyline and deprenyl; catechol-O-methyl transferase in inhibited by agents such as tropolone.

As applied to this invention, an agonist of a neurochemical is a different compound that mimics the action of the neurochemical in the retinal tissue; an antagonist of the neurochemical is a compound that opposes or blocks action of the neurochemical on the retinal tissue. Although ocular administration is described herein and is generally preferred, systemic administration may also be employed under suitable circumstances.

Because of the relationship of biogenic amines to hypertension and cardiac function, there has been considerable interest in these compounds. A great number of related drugs have been synthesized and brought to market. Among the better known drugs identified as dopamine agonists or antagonists are:

| Dopamine Receptor Agonists | Dopamine Receptor Antagonists |
| --- | --- |
| lergotrile | domperidone |
| pergolide | metoclorpromide |
| dipropyldopamine | sulpiride |
| N-methyldopamine | haloperidol |
| bromocriptine | bulbocapnine |
| apomorphine | spiroperidol |
| 2-bromo-α-ergocryptine | thioproperazine |
| dihydroergocryptine | fluphenazine |
| lisuride | pimozide |
| R(−)n-propylnor-apomorpine HCl | spiperone |

In addition, there are many other agents with similar properties that are currently identified only by the individual drug company code number.

Despite notable differences in anatomy between the eyes of primates and those of birds, image deprivation-induced myopia which is induced in chickens closely resembles that in the primate as shown by studies made on chicks and young monkeys. In both species, evidence suggests that control for postnatal ocular growth is substantially local, within the eye, apparently originating at the retina. Because the chicken matures quickly, it was used extensively in studies made in connection with this invention.

This invention is now described in and by the following specific example thereof.

EXAMPLE 1

Form-deprivation myopia was induced in day-old White Leghorn chicks under aseptic conditions and ether anesthesia using one of three uniocular procedures: eyelid suture, translucent plastic goggle or transparent but image-degrading plastic goggle. Maintained on a 12 hour light:dark cycle, the birds were killed at ages up to 4 weeks by decapitation for biochemical studies or by perfusion for histochemical studies with Zamboni's fixative under deep pentobarbital anesthesia. Axial and equatorial dimensions of unfixed eyes were measured with vernier calipers. For biochemistry, retinas were sonicated in cold $0.1N$ $HClO_4$ and analyzed by high performance liquid chromatography with electrochemical detection (Iuvone et al., Brain Res. 418:314–324, 1987). For histochemistry, retinas were processed either by the formaldehyde-induced-fluorescence technique for catecholamines or by indirect immunohistochemistry for serotonin.

Unilateral visual deprivation by lid suture, translucent goggle or transparent goggle resulted in excessive eye growth in both axial and equatorial dimensions. All three types of visual deprivation also reduced retinal concentrations of dopamine (3,4-dihydroxyphenethylamine) and its metabolite 3,4 dihydroxyphenylacetic acid (DOPAC), as measured in light adapted birds at intervals during a four-week observation period. In contrast, no orderly change in retinal concentration of serotonin and its metabolite 5-hydroxyindoleacetic acid (5 HIAA) was found in the same birds (data not shown). Normally, retinal concentrations of dopamine and DOPAC vary in accordance with the state of light/dark adaptation. Visual deprivation by translucent goggles for two weeks lessened the usual light-induced rise.

To elucidate the metabolic alteration underlying the observation, light-adapted birds visually deprived by unilateral translucent goggle were studied at two weeks. The conversion of DOPA (2-amino-3-(3,4-dihydroxyphenyl) propanoic acid) to dopamine was blocked by administering m-hydroxybenzylhydrazine (150 mg/kg IP), an inhibitor of aromatic amino acid decarboxylase. Thirty minutes later, the DOPA concentration in visually deprived retinas (0.22±0.01 ng/mg protein) was half that measured in contralateral eyes (0.43±0.03 ng/mg protein; p 0.001, using t-statistics on the paired differences; n=9) indicating a decreased rate of dopamine synthesis.

Histochemical observations paralleled the biochemical results. In comparison of control and deprived contralateral eyes by the formaldehyde-induced-fluorescence technique for catecholamines, the overall fluorescence intensity of the retina tended to be greater in control eyes compared to contralateral eyes visually deprived by lid suture both at two or four weeks. In these preparations, there was no difference in distribution of fluorescent dopaminergic amacrine cells and their processes. In other experiments there was no difference in immunohistochemical reactivity of the retina for serotonin in comparing control to similarly deprived contralateral eyes (data not shown).

In accordance with this invention, we administered either apomorphine or haloperidol, a dopamine agonist and antagonist respectively; each shows relative non-selectivity for the D-1 and D-2 dopamine receptor subtypes. These agents were administered daily for two weeks to the eye visually deprived by lid suture. Each agent alone selectively lessened the expected axial elongation, but neither altered the exaggerated equatorial growth occurring beneath the lid suture. Of the two agents, apomorphine was the more powerful. In fact at the highest concentration, apomorphine blocked excess axial elongation completely. Administration of a mixture of the two drugs nullified the effect of each: exaggerated axial growth proceeded unchecked in the deprived eye.

Additionally, in follow-up experiments a second dopamine agonist, n-propylnorapomorphine, when used alone had a similar effect as apomorphine in checking axial elongation of the eye (see Table II).

TABLE I

Effect of drug therapy on the growth of lid sutured chick eyes.

| | | Changes in Ocular Dimensions (Deprived Eye minus Control Eye) | | |
|---|---|---|---|---|
| Drug | Dose (ng) | Axial Length (mm) | Equatorial Diameter (mm) | n |
| Apomorphine | 250 | −0.01 ± 0.06 | 0.83 ± 0.09 | 15 |
| Apomorphine | 25 | 0.07 ± 0.09 | 0.99 ± 0.06 | 11 |
| Apomorphine | 2.5 | 0.17 ± 0.5 | 0.81 ± 0.08 | 7 |
| Haloperidol | 300 | 0.18 ± 0.06 | 0.94 ± 0.09 | 15 |
| Haloperidol | 30 | 0.13 ± 0.08 | 0.99 ± 0.06 | 10 |
| Haloperidol | 3 | 0.17 ± 0.12 | 0.93 ± 0.08 | 6 |
| Apomorphine plus Haloperidol | 25 30 | 0.51 ± 0.18 | 0.91 ± 0.09 | 8 |
| Saline control | — | 0.36 ± −0.18 | 0.87 ± 0.08 | 13 |

Following unilateral lid suture in newborn chicks, apomorphine, haloperidol, or saline was administered daily to the deprived eye. In all instances, the contralateral control eye received saline vehicle. All agents were given under ether anesthesia by subconjunctival injection, a highly effective method of obtaining ocular drug penetration.

Based on a one-way analysis of variance, there is a significant treatment effect on axial length (p 0.0002 for the apomorphine treatment groups vs. control; p 0.002 for the haloperidol treatment groups vs. control), but there is no significant treatment effect on equatorial diameter. There is no statistically significant difference comparing the apomorphine to the haloperidol treatment groups. The proportion of variability in axial length due to treatment is 25%; that in equatorial length is 4%. Tukey's studentized range test at the 0.05 level identifies significant differences for the saline control vs. apomorphine (250 ng), for the combined apomorphine/haloperidol vs. apomorphine (250 ng) and for the combined apomorphine/haloperidol vs. apomorphine (25 ng) treatment groups.

Thus, deprivation of form vision in the newborn chick simultaneously perturbs ocular growth and retinal dopamine metabolism. Reduced retinal dopamine in deprived eyes is observable only during light adaptation and is associated with a decrease in dopamine biosynthesis. Administration of the dopamine-related drug apomorphine or haloperidol to an eye can reduce and sometimes even rectify the exaggerated axial growth that accompanies visual deprivation by lid suture. The effect is selective as neither agent corrects the exaggerated equatorial growth that occurs simultaneously.

EXAMPLE 2

As shown on Table II a series of follow-on studies in chick have performed. The identical protocol was used. One eye received lid suture, one eye was open. Either drug or saline was administered to the sutured eye; the open eye received saline. We assessed the effects of specific drugs or drug combinations on the exaggerated ocular growth that occurs beneath a lid suture. Most important in these studies, our original result has been repeatedly confirmed. Further, evidence has been uncovered for activity in our test system of drugs affecting both recognized dopamine receptor subtypes, now generally called D1 and D2.

Reviewing Table II, it is apparent that the apomorphine analog, N-propyl norapomorphine, mimics the original apomorphine result in retarding the expected axial elongation of the lid-sutured eye.

Turning to the D1 receptor system, the agent R(+)-SKF 38393 hydrochloride (R(+)-1-Phenyl-2,3,4,5-tetrahydro-(1H)-3-benzazepine-7,8-diol hydrochloride known to be a D1 selective agonist acts at the two higher doses as does apomorphine to block axial elongation. When the D1 receptor is assessed through the use of the nonspecific agonist apomorphine in combination with a specific antagonist to the D2 receptor, spiperone, again a definite but moderate attenuation of expected axial elongation is observed.

The D1 receptor subtype typically acts by stimulating the intracellular production of cyclic adenosine monophosphate (AMP). When the receptor system itself is bypassed by use of forskolin, a substance known to increase directly the intracellular production of cyclic AMP, again an attenuation of the expected axial elongation is observed. In this respect forskolin acts as a compound that, broadly, mimics the action of the neurochemical on the retinal tissue.

When instead the D2 receptor system is surveyed, evidence for activity is also found. In this instance, the drug quinpirole attenuates the axial elongation at a dose of 0.205 μg. When the D2 receptor is assessed instead by using a combination of the nonspecific agonist apomorphine with the specific D1 antagonist R(+)-SCH 23990 hydrochloride, R(+)-CHMB (R(+)-7-Chloro-8-hydroxy-3-methyl-1-phenyl-2,3,4,5-tetrahydro-1H-

3benzazepine HCI), again a similar attenuation of axial elongation is observed. Lastly, 2-bromo-A-ergocryptine methanesulfonate salt known to be mainly a D2 system agonist also yields an attenuation of axial elongation, in this instance only at the higher doses.

In summary, the series of follow-on studies repeatedly confirm the original work and show that dopaminergic drugs reduce the expected axial elongation of the eye that follows visual deprivation. The available data do not enable one to distinguish within the dopamine system whether the effects are primarily of the D1 and D2 receptor type; instead they suggest that each may be involved. Alternatively, the results may derive from interactions within these subsystems or from varying degrees of nonspecificity of the drugs used, a phenomenon that is well acknowledged.

TABLE II

Effect of drug therapy on the growth of lid-sutured chick eyes.

| Drug | Dose (μg) | Axial Length (mm) | Equatorial (mm) | n |
|---|---|---|---|---|
| R(−)Propylnor apomorphine HCl | 2.65 | 0.13 ± 0.10 | 0.74 ± 0.05 | 9 |
|  | 0.265 | 0.13 ± 0.10 | 0.91 ± 0.05 | 7 |
| R(+)-SKF-38393 HCl | 23.5 | 0.23 ± 0.13 | 0.89 ± 0.08 | 7 |
|  | 2.35 | 0.13 ± 0.05 | 0.89 ± 0.05 | 22 |
|  | 0.235 | 0.53 ± 0.08 | 1.09 ± 0.02 | 5 |
| Apomorphine + spiperone | 2.5 30.0 | 0.25 ± 0.13 | 1.02 ± 0.10 | 8 |
|  | 2.5 3.0 | 0.18 ± 0.08 | 0.74 ± 0.05 | 7 |
|  | 0.25 0.3 | 0.18 ± 0.08 | 0.84 ± 0.10 | 7 |
| Forskolin | 2.5 | 0.13 ± 0.05 | 0.86 ± 0.10 | 10 |
| Quinpirole | 20.5 | 0.30 ± 0.10 | 1.04 ± 0.08 | 8 |
|  | 2.05 | 0.33 ± 0.08 | 0.79 ± 0.10 | 7 |
|  | 0.205 | 0.05 ± 0.05 | 0.91 ± 0.05 | 7 |
| Apomorphine + R(+)-Sch 23390 HCl | 2.5 25.0 | 0.18 ± 0.08 | 0.96 ± 0.13 | 7 |
|  | 2.5 2.5 | 0.18 ± 0.05 | 0.66 ± 0.05 | 7 |
|  | 0.25 0.25 | 0.15 ± 0.10 | 0.96 ± 0.13 | 7 |
| 2-Bromo-A-Ergocryptine Methanesulfonate Salt | 6.0 | 0.10 ± 0.10 | 0.94 ± 0.08 | 9 |
|  | 0.6 | 0.33 ± 0.13 | 0.94 ± 0.08 | 6 |
| Saline Control | — | 0.35 ± 0.03 | 0.84 ± 0.05 | 32 |

EXAMPLE 3

The following postnatal treatment suitable to prevent or inhibit the abnormal postnatal axial ocular growth in primates, monkeys and perhaps humans, was conducted: A one-percent sterile solution of apomorphine HCl was prepared for topical use. For the pilot study in the monkey, the vehicle contained 2.2% glycerol and 97.8% water (vol/vol); this solution was used both to dissolve the apomorphine and also without drug as the control eye drop. The apomorphine solution was prepared as a 1% (weight/volume) solution.

Eight newborn monkeys were unilaterally occluded through application of an opaque contact lens to one eye. In four monkeys (controls), both eyes received 2 drops of vehicle to each eye twice a day for approximately 3 months and subsequently 3 times a day for approximately 3 months. In four monkeys (treated), the occluded eye received 2 drops of one percent apomorphine solution twice a day for 3 months and then 3 times a day for 3 months, and the other eye received the same number of drops of vehicle alone at the same time. A dramatic result confirmatory of the chick findings has been obtained. Specifically, not one out of the four monkeys eyes treated with apomorphine developed the expected axial elongation whereas three out of four control monkeys developed axial elongation in the occluded eye.

Pertinent recent observations have also been made on retinal neuropeptides in experimental myopia of primates. Like the selective alteration in retinal dopamine but not serotonin that accompanies form deprivation myopia in the chick, lid fusion induces a selective alteration of vasoactive intestinal polypeptide but not substance P in retinal amacrine cells of the monkey. There the amount of one retinal neuropeptide is found to be increased under conditions inducing experimental myopia. The state of catecholamines in primate myopia is now known to parallel changes already described in the chick. The state of neuropeptides in avian myopia is currently unknown.

It is possible that the same neurochemical process described herein, perhaps in different direction and/or degree, is involved in the diminished postnatal ocular axial growth resulting in hyperopia. It is suggested that similar excesses or deficiencies of retinal neurochemicals are involved during hyperopia development. As a consequence, treatment for hyperopia can involve the administration of effective amounts of said neurochemical, its agonist or antagonist.

Given the above-described effects of image deprivation on postnatal ocular growth with the consequent changes in neurochemical concentrations in the retina, it may be that controlled light exposure may be used alone or in conjunction with the herein described drug therapy to alter the balance of ocular neurochemicals favorably. Such controlled exposure may include timed, intermittent light exposure, change of day-night daily regimen and/or ratios, and the use of eye glasses that control such exposure. Eye exercises that are found to affect the ocular neurochemical balance may also be used in conjunction with this invention.

We claim:

1. A method of controlling the abnormal postnatal growth of the eye of a maturing animal which comprises controlling the presence of a neurochemical, or its agonist, or its concentration of which neurochemical is found to be changed under conditions during maturation ordinarily leading to abnormal axial length.

2. A method of controlling the abnormal postnatal growth of the eye of a maturing animal which comprises the ocular administration of effective amounts of a neurochemical, its agonist or its antagonist, the concentration of which neurochemical is found to be changed under conditions during maturation ordinarily leading to abnormal axial length.

3. The method of claim 1 wherein the neurochemical dopamine is reduced during maturation and an therapeutically effective amount of a dopamine agonist is used for said ocular administration.

4. The method of claim 3 wherein the neurochemical is dopamine and the agonist is apomorphine.

5. A method of inhibiting the abnormal postnatal axial growth of the eye of a maturing animal during conditions ordinarily leading to said abnormal growth, which comprises (1) determining the neurochemical present in the retina of said eye, the concentration of which is reduced during said conditions, and (2) administering to said eye during postnatal maturation therapeutically effective amounts of said neurochemical, or its agonist.

6. The method of claim 5 wherein the neurochemical reduced during maturation is dopamine and an therapeutically effective amount of a dopamine agonist is used for said ocular administration.

7. The method of claim 5, wherein the neurochemical is dopamine and the agonist is apomorphine.

8. A method of inhibiting the abnormal postnatal axial growth of the eye of a maturing bird or primate which comprises the ocular administration of a pharmaceutically effective amount of an agonist for dopamine.

9. The method of claim 8 wherein the agonist is apomorphine.

10. The method of claim 3 wherein the neurochemical is dopamine and the agonist is R(+)-1-phenyl-2,3,4,5-tetrahydro-(1H)-3-benzazepine-7,8-diol hydrochloride.

11. The method of claim 3 wherein the neurochemical is dopamine and the agonist is quinpirole.

12. The method of claim 5 wherein the neurochemical is dopamine and the agonist is R(+)-1-phenyl-2,3,4,5-tetrahydro-(1H)-3-benzazepine-7,8-diol hydrochloride.

13. The method of claim 5 wherein the neurochemical is dopamine and the agonist is quinpirole.

14. The method of claim 8 wherein the agonist is selected from the group consisting of R(+)-1-phenyl-2,3,4,5-tetrahydro-(1H)-3-benzazepine-7,8-diol hydrochloride and quinpirole.

* * * * *

UNITED STATES PATENT AND TRADEMARK OFFICE
CERTIFICATE OF CORRECTION

PATENT NO. : 5,284,843
DATED : February 8, 1994
INVENTOR(S) : Richard A. Stone, Alan M. Laties, Paul M. Iuvone It is certified that error appears in the above-indentified patent and that said Letters Patent is hereby corrected as shown below:

In Column 1, line 10, after which, insert ⊥

In Column 3, line 32, after e.g., change "δ" to ϒ

In Column 7, line 23 (in Table II), under Dose, change "(µg)" to µg

In Column 7, line 53, before was, change "HCI" to HCl

In Column 8, line 46, after agonist, change "or its" to [or its]

In Column 8, line 52, after of, insert therapeutically

In Column 8, line 53, after neurochemical, insert or

In Column 8, line 53, after agonist, change "or its antagonist," to [or it antagonist,]

Signed and Sealed this

Twenty-seventh Day of September, 1994

Attest:

BRUCE LEHMAN

*Attesting Officer*        *Commissioner of Patents and Trademarks*